United States Patent [19]
Ruddy et al.

[11] Patent Number: 5,472,682
[45] Date of Patent: * Dec. 5, 1995

[54] COMPOSITIONS OF IODOPHENYL ESTERS AND IODOPHENYL SULFONATES AND PHARMACEUTICALLY ACCEPTABLE CLAYS FOR VISUALIZATION OF THE GASTROINTESTINAL TRACT

[75] Inventors: Stephen B. Ruddy, Schwenksville; Mary E. Roberts, Downingtown; Gregory L. McIntire, West Chester; Eugene R. Cooper, Berwyn; Kimberly G. Estep, Pottstown, all of Pa.

[73] Assignee: Sterling Winthrop Inc., New York, N.Y.

[*] Notice: The portion of the term of this patent subsequent to Jun. 7, 2011, has been disclaimed.

[21] Appl. No.: 249,424

[22] Filed: May 26, 1994

Related U.S. Application Data

[63] Continuation-in-part of Ser. No. 229,048, Apr. 18, 1994, Pat. No. 5,385,722, which is a continuation-in-part of Ser. No. 40,823, Mar. 31, 1993, Pat. No. 5,318,769.

[51] Int. Cl.$^6$ .......................... A61K 49/04; A61K 31/22
[52] U.S. Cl. .......................... 424/9.45; 514/57; 514/546; 514/548; 514/552
[58] Field of Search ............................ 424/5, 4, 9.45; 560/121, 125, 126, 129, 174, 184, 187; 514/57, 546, 548, 552

[56] References Cited

U.S. PATENT DOCUMENTS

| | | | |
|---|---|---|---|
| 2,348,231 | 5/1944 | Strain et al. | 424/5 |
| 2,622,100 | 12/1952 | Newbery et al. | 260/612 |
| 3,360,436 | 12/1967 | Felder et al. | 167/95 |
| 3,361,700 | 1/1968 | Archer et al. | 167/95 |
| 3,574,718 | 4/1971 | Bjork et al. | 260/501.11 |
| 3,795,698 | 3/1974 | Soulal et al. | 260/471 OR |
| 3,825,591 | 7/1974 | Felder et al. | 260/519 |
| 4,692,325 | 9/1987 | Kritzler | 424/4 |
| 4,835,304 | 5/1989 | Williams | 560/144 |
| 4,927,624 | 5/1990 | Bryant et al. | 424/9 |
| 5,107,842 | 5/1992 | Levene et al. | 128/662.02 |
| 5,277,896 | 1/1994 | Balkus, Jr. | 424/9 |
| 5,318,769 | 6/1994 | Bacon et al. | 424/5 |
| 5,360,604 | 11/1994 | Ruddy et al. | 424/5 |
| 5,385,722 | 1/1995 | Baker et al. | 424/5 |

FOREIGN PATENT DOCUMENTS 1259565  9/1989  Canada.
1481943  5/1967  France.

OTHER PUBLICATIONS

Yoshikawa et al, Chem. Abstr. 70 (10):3539, pp. 318–319 (1969).

Primary Examiner—Gary E. Hollinden
Attorney, Agent, or Firm—Fish & Richardson

[57] ABSTRACT

Disclosed are x-ray contrast compositions of the formula $$\underset{I_n \quad Z_y}{\text{Ar}}(OXR)_w$$

wherein

X is $$-\overset{\overset{\displaystyle O}{\|}}{C}- \text{ or } -SO_2-;$$

Z is H, halo, methyl, ethyl, n-propyl, $C_4$-$C_{20}$ alkyl, cycloalkyl, lower alkoxy, cyano, where the alkyl and cycloalkyl groups can be substituted with halogen or halo-lower-alkyl groups;

R is $C_1$-$C_{25}$ alkyl, cycloalkyl or aryl each of which may be optionally substituted with halo, fluoro-lower-alkyl, lower-alkoxy, hydroxy, carboxy or lower-alkoxy carbonyl; lower-alkenyl, lower-alkynyl, lower-alkylene or lower-alkoxy-carbonyloxy;

n is 1–5;

y is 0–4; and w is 1–4;

in combination with a pharmaceutically acceptable clay; and method for their use in diagnostic radiology of the gastrointestinal tract.

24 Claims, No Drawings

COMPOSITIONS OF IODOPHENYL ESTERS AND IODOPHENYL SULFONATES AND PHARMACEUTICALLY ACCEPTABLE CLAYS FOR VISUALIZATION OF THE GASTROINTESTINAL TRACT

This application is a continuation-in-part of application Ser. No. 08/229,048, now U.S. Pat. No. 5,385,722, filed on Apr. 18, 1994, which in turn is a continuation-in-part of application Ser. No. 08/040,823, filed on Mar. 31, 1993, now U.S. Pat. No. 5,318,769.

BACKGROUND OF THE INVENTION

1. Field of the Invention

This invention relates to aqueous compositions containing the contrast agents iodophenyl esters and/or iodophenyl sulfonates, in combination with pharmaceutically acceptable clays, and methods for their use in diagnostic radiology of the gastrointestinal tract.

2. Reported Developments

Roentgenographic examination utilizing x-rays and computed tomography (hereinafter CT) scans of fractures and other conditions associated with the skeletal system is routinely practiced without the use of contrast agents. X-ray visualization of organs containing soft tissue, such as the gastrointestinal (hereinafter GI) tract, requires the use of contrast agents which attenuate x-ray radiation. D. P. Swanson et al in "Pharmaceuticals In Medical Imaging", 1990, MacMillan Publishing Company, provides an excellent background in medical imaging utilizing contrast agents and compositions therewith.

Roentgenographic examination of the GI tract are indicated for conditions of digestive disorders, changes in bowel habit, abdominal pain, GI bleeding and the like. Prior to radiological examination, administration of a radiopaque contrast medium is necessary to permit adequate delineation of the respective lumen or mucosal surface from surrounding soft tissues. Accordingly, a contrast medium is administered orally to visualize the mouth, pharynx, esophagus, stomach, duodenum and proximal small intestine. The contrast medium is administered rectally for examination of the distal small intestine and the colon.

The most widely used contrast agent for the visualization of the GI tract is barium sulfate administered as a suspension orally or rectally as an enema. (See, for example, U.S. Pat. Nos.: 2,659,690; 2,680,089; 3,216,900; 3,235,462; 4,038,379 and 4,120,946) Notwithstanding its relatively good contrast characteristics, negligible absorption from the GI tract following oral or rectal administration and speedy excretion from the body, barium sulfate has certain disadvantages. In the presence of intestinal fluids it lacks homogeneity and poorly adheres to mucus membranes which can result in poor x-ray images. In the colon, when administered as an enema, it flocculates and forms irregular clumps with fecal matter.

Iodinated organic compounds have also been used as GI contrast agents since the iodine atom is an effective x-ray absorber. They have the most versatility and are utilized in the widest variety of procedures. They are very absorptive of x-rays with which the iodine interacts and produce a so-called photoelectric effect which is a large magnification in contrast caused by the photons stopped in the iodine-containing medium. The magnification of contrast exceeds the level that would be expected from relative changes in density. Because of this magnification, relatively low concentrations of the contrast agent can be utilized. (For iodinated agents see, for example, U.S. Pat. Nos.: 2,786,055; 3,795,698; 2,820,814; 3,360,436; 3,574,718, 3,733,397; 4,735,795 and 5,047,228.)

The desiderata for an ideal GI contrast agent includes: good toxicological profile; the ability to fill the entire bowel/lumen and evenly coat the gut mucosa so that the presence of the bowel is detectable when the lumen is not distended; and nonirritation to the intestinal mucosa; and passage through the GI tract without producing artifacts or stimulating vigorous intestinal peristalsis.

These requirements were addressed by many investigators and their efforts resulted in great improvements over the years. The requirement of evenly coating the gut mucosa with a contrast agent to effectively cover the walls of the intestines proved to be rather difficult. Without meeting these requirements it is impossible to obtain x-ray pictures of high precision. To that end, the use of certain polymer additives were proposed as illustrated hereunder.

U.S. Pat. No. 4,069,306 discloses an x-ray contrast preparation which is said to adhere to the walls of body cavities. The preparation comprises a finely divided water-insoluble inorganic x-ray contrast agent and minute particles of a hydrophilic polymer which is insoluble in water but is water-swellable. The body cavity is supplied with such preparation suspended in water. The x-ray contrast agent is present in admixture with and/or enclosed in and/or adhered to said minute polymer particles.

U.S. Pat. No. 4,120,946 discloses a pharmaceutical composition for barium opacification of the digestive tract, comprising colloidal barium sulfate and a polyacrylamide in an aqueous vehicle. The polyacrylamide forms a viscous solution at low concentration which makes it possible to maintain the barium sulfate in suspension and at the same time permit good adherence of the preparation to the walls of the organ which it is desired to x-ray.

U.S. Pat. No. 5,019,370 discloses a biodegradable radiographic contrast medium comprising biodegradable polymeric spheres which carry a radiographically opaque element, such as iodine, bromine, samarium and erbium. The contrast medium is provided either in a dry or liquid state and may be administered intravenously, orally and intraarterially.

While these polymeric materials greatly enhance attachment of the contrast agent used therewith to the walls of organs for better visualization thereof, they do not provide a uniform coating thereon. As such, there is still a need for an improved x-ray imaging medium that uniformly coats the soft tissues subjected to diagnostic x-ray examination.

We have now discovered that certain iodophenyl esters and iodophenyl sulfonates in combination with pharmaceutically acceptable clays provide excellent x-ray imaging medium.

SUMMARY OF THE INVENTION

It is the object of the present invention to provide compositions for coating the gastrointestinal tract of mammals to form an effective radiopaque coating thereon by which diagnostic examination of the GI tract may be accomplished. To that end, a thin coating is formed on the inner surface of the GI tract effected by ingesting, prior to visualization by an x-ray emitting device, a composition containing a pharmaceutically acceptable clay and an x-ray contrast agent. Such compositions must meet several requirements: both the x-ray contrast agent and the clay must be nontoxic; must not contain leachable or digestible components that would deleteriously affect the patient; and no components of the coating should be absorbed by, and pass through, the inner surface of the intestine.

The contrast agent and the pharmaceutically acceptable clay are incorporated in a liquid media for administration to a mammal for x-ray visualization of the GI tract.

The x-ray contrast agent of the present invention is of the formula:

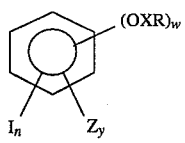

wherein
X is

or $-SO_2-$;

Z is H, halo, methyl, ethyl, n-propyl, $C_4$-$C_{20}$ alkyl, cycloalkyl, lower alkoxy, cyano, where the alkyl and cycloalkyl groups can be substituted with halogen or halo-lower-alkyl groups;

R is $C_1$-$C_{25}$ alkyl, cycloalkyl or aryl each of which may be optionally substituted with halo, fluoro-lower-alkyl, lower-alkoxy, hydroxy, carboxy or lower-alkoxy carbonyl; lower-alkenyl, lower-alkynyl, lower-alkylene or lower-alkoxy-carbonyloxy;

n is 1–5;
y is 0–4; and
w is 1–4.

As used herein, the term halogen (or halo) means fluorine, chlorine, bromine or iodine.

As used herein, the term cycloalkyl means carbocyclic rings having from three to eight ring carbon atoms including cyclopropyl, cyclobutyl, cyclopentyl, cyclohexyl and cyclooctyl which may be substituted on any ring carbon atom thereof by one or more lower-alkyl groups, lower-alkoxy groups or halogens.

As used herein the terms lower-alkyl and lower-alkoxy mean monovalent aliphatic radicals, including branched chain radicals, of from one to ten carbon atoms. Thus, the lower-alkyl moiety of such groups include, for example, methyl, ethyl, propyl, isopropyl, n-butyl, sec-butyl, t-butyl, n-pentyl, 2-methyl-3-butyl, 1-methylbutyl, 2-methylbutyl, neopentyl, n-hexyl, 1-methylpentyl, 3-methylpentyl, 1-ethylbutyl, 2-ethylbutyl, 2-hexyl, 3-hexyl, 1,1,3,3-tetramethylpentyl, 1,1-dimethyloctyl and the like.

As used herein, the term lower-alkenyl and lower-alkynyl means monovalent, unsaturated radicals including branched chain radicals of from three to ten carbon atoms and thus include 1-ethenyl, 1-(2-propenyl), 1-(2-butenyl), 1-(1-methyl-2-propenyl), 1-(4-methyl-2-pentenyl), 4,4,6-trimethyl-2-heptenyl, 1-ethynyl, 1-(2-propynyl), 1-(2-butynyl), 1-(1-methyl-2-propynyl), 1-(4-methyl-2-pentynyl) and the like.

As used herein, the term alkylene means divalent saturated radicals, including branched chain radicals of from two to ten carbon atoms having their free valences on different carbon atoms and thus includes 1,2-ethylene, 1,3-propylene, 1,4-butylene, 1-methyl-1,2-ethylene, 1,8-octylene and the like.

As used herein, the term aryl means an aromatic hydrocarbon radical having six to ten carbon atoms. The preferred aryl groups are phenyl, substituted phenyl and naphthyl substituted by from one to three, the same or different members of the group consisting of lower-alkyl, halogen, hydroxy-lower-alkyl, alkoxy-lower-alkyl and hydroxy.

The x-ray contrast compound can comprise one, two, three or more iodine atoms per molecule; preferred species contain at least two, and more preferably, at least three iodine atoms per molecule.

The solid x-ray contrast agents in particulate forms useful in the practice of the present invention can be prepared by techniques known in the art. The solid agents are comminuted to the desired size using conventional milling methods, such as airjet or fragmentation milling. We have found that an effective average particle size of less than about 100μ provides for good distribution and coating in the GI tract. As used herein, particle size refers to a number average particle size as measured by conventional techniques, such as sedimentation field flow fractionation and disk centrifugation. An effective average particle size of less than about 100μ means that at least about 90% of the particles have a weight average particle size of less than about 100μ as measured by art recognized techniques.

The natural clays incorporated in the compositions of the present invention are selected from the group consisting of montmorillonite, beidelite, nontronite, hectorite and saponite.

A method for diagnostic imaging of the GI tract for use in medical procedures in accordance with this invention comprises orally or rectally administering to the mammalian patient in need of x-ray examination, an effective contrast producing amount of a composition of the present invention. After administration, at least a portion of the GI tract containing the administered composition is exposed to x-rays to produce an x-ray image pattern corresponding to the presence of the contrast agent, then the x-ray image is visualized and interpreted using techniques known in the art.

DETAILED DESCRIPTION OF THE INVENTION

Compounds of the present invention can be made according to the schematic procedure shown or other methods using commercially available starting materials, intermediates and reagents. Starting materials, reagents and solvents can be obtained from chemical suppliers such as Aldrich, Baker and Eastman Chemical Companies, or they may be prepared by techniques known in the art.

Scheme 1

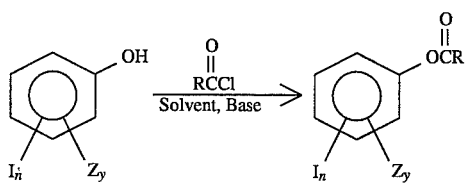

wherein Z, R, n and y are as previously described.

The following examples will further illustrate the compounds used in the present invention.

EXAMPLE 1
2,4,6-Triiodophenyl 2-ethylhexanoate

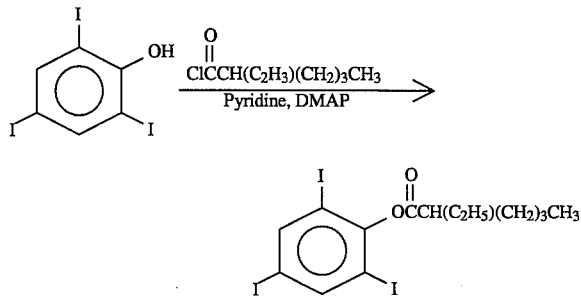

A solution of 2,4,6-triiodophenol (20.0 g, 42 mmol), 2-ethylhexanoyl chloride (25 ml, 144 mmol, 3.5 eq.) and 4-dimethylaminopyridine (DMAP; 2 mmol, 250 mg, 0.05 eq.) in 150 ml of pyridine was stirred overnite at room temperature. The solution was poured into 1000 ml of 1 N aqueous hydrochloric acid and the aqueous solution was extracted twice with ethyl acetate. The combined organic layers were washed with aqueous hydrochloric acid, water, saturated aqueous sodium chloride and then dried over magnesium sulfate. The ethyl acetate solution was then concentrated under vacuum to give an oil (30 g) which was purified by silica gel chromatography (5% ethyl acetate/hexanes eluent) to give the product. Concentration under high vacuum afforded 21 g (79%) of the desired hexanoate ester as an oil. The product was taken up in hexanes and filtered through a pad of basic alumina. The flitrate was concentrated under high vacuum to give 16.9 g of analytically pure product.

Title Compound: $^1$H (300 MHz) and $^{13}$C (75 MHz) NMR spectra were consistent with the desired structure. Calculated for $C_{14}H_{17}I_3O_2$: C, 28.12; H, 2.87; I, 63.66. Found: C, 28.27; H, 2.79; I, 63.62.

EXAMPLE 2
2,4,6-Triiodophenyl 2-methylpentanoate

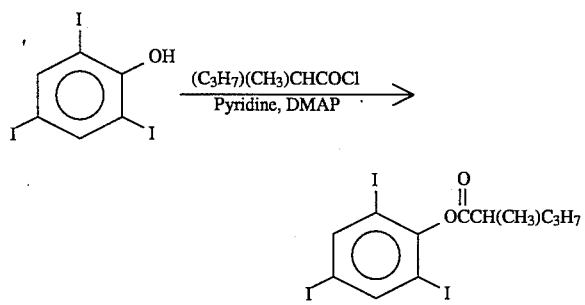

Using the procedure described for the synthesis of 2,4,6-triiodophenyl (2-ethyl)hexanoate, 2,4,6-triiodophenyl 2-methylpentanoate was prepared in 25% yield as a solid, mp. 66°–68° C., from 2,4,6-triiodophenol (15.0 g, 31.8 mmol), 2-methylvaleryl chloride (4.6 g, 34.2 mmol, 1.07 eq.) and a catalytic amount (0.1 g) of 4-dimethylaminopyridine in dry pyridine (20 ml).

Title Compound: $^1$H (300 MHz) and $^{13}$C (75 MHz) NMR spectra were consistent with the desired structure. Calculated for $C_{12}H_{13}I_3O_2$: C, 25.29; H, 2.30; I, 66.80. Found: C, 25.36; H, 2.13; I, 66.57.

EXAMPLE 3
2,4,6-Triiodophenyl 3-cyclopentyl propionate

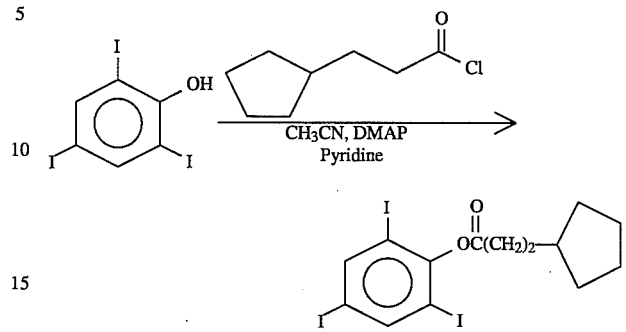

A solution of 2,4,6-triiodophenol (15.0 g, 31.8 mmol), 3-cyclopentylpropionyl chloride (14.6 ml, 95.4 mmol, 3 eq), pyridine (2.83 ml, 35.0 mmol, 1.1 eq) and 4-dimethylaminopyridine (200 mg) in 150 ml of acetonitrile was heated to reflux under argon for 21 hrs and then cooled. The reaction solution was washed with water, saturated aqueous sodium chloride and then dried over magnesium sulfate. The organic layer was filtered and concentrated under vacuum. The resulting residue was purified by silica gel chromatography (1% ethyl acetate/hexanes) to give 19.17 g of solid product. The solid was recrystallized from hexanes to give the final product as a feathery white solid.

Title Compound: $^1$H (300 MHz) and $^{13}$C (75 MHz) NMR spectra were consistent with the desired structure. Calculated for $C_{14}H_{15}I_3O_2$: C, 28.21; H, 2.54; I, 63.88. Found: C, 28.25; H, 2.44; I, 64.06.

EXAMPLE 4
2,4,6-Triiodophenyl (2-propyl)pentanoate

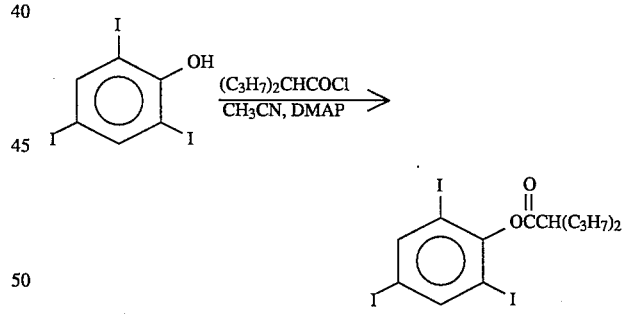

A mixture of 2,4,6-triiodophenol (2.0 g, 4.24 mmol), 2-propylvaleroyl chloride (2.5 ml, 12.7 mmol, 3 eq) and 4-dimethylaminopyridine (DMAP; 20 mg) in 20 ml of acetonitrile was refluxed under argon overnite. The reaction mixture was cooled and poured into excess aqueous sodium bicarbonate and then extracted with dichloromethane. The dichloromethane extract was dried over magnesium sulfate, filtered, and evaporated to give the crude product (2.42 mmol, 95%) as a pink solid. Recrystallization from ethyl acetate gave 1.75 g (68%) of pure product, mp 99°–101° C.

Title Compound: $^1$H (300 MHz) and $^{13}$C (75 MHz) NMR spectra were consistent with the desired structure. Calculated for $C_{14}H_{17}I_3O_2$: C, 28.12; H, 2.87; I, 63.66. Found: C, 28.35; H, 2.80; I, 63.74.

EXAMPLE 5
2,4,6-Triiodophenyl perfluoroheptanoate

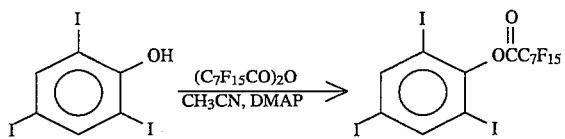

A mixture of 2,4,6-triiodophenol (2.0 g, 4.24 mmol), perfluoroheptanoic anhydride (10.3 g, 12.7 mmol, 3 eq) and 4-dimethylaminopyridine (DMAP; 20 mg) in 20 ml of acetonitrile was heated to reflux under argon for 5 hrs. On cooling, the resulting solution separated into two layers whereupon the lower layer solidified. The solids were collected and the flitrate was poured into excess saturated aqueous sodium bicarbonate. The aqueous mixture was extracted with dichloromethane; the organic layer was dried over magnesium sulfate, filtered and concentrated in vacuo to give an off-white solid. The solid was recrystallized from methanol to give the desired product (0.51 g, 14%) as white needles, mp 71°–73° C.

Title Compound: $^1$H (300 MHz) and $^{13}$C (75 MHz) NMR spectra were consistent with the desired structure. Calculated for $C_{14}H_2F_{15}I_3O_2$: C, 19.38; H, 0.23; I, 43.87. Found: C, 19.16; H, 0.02; I, 43.78.

EXAMPLE 6
2,4,6-Triiodophenyl-tris-(2-ethyl)-hexanoate

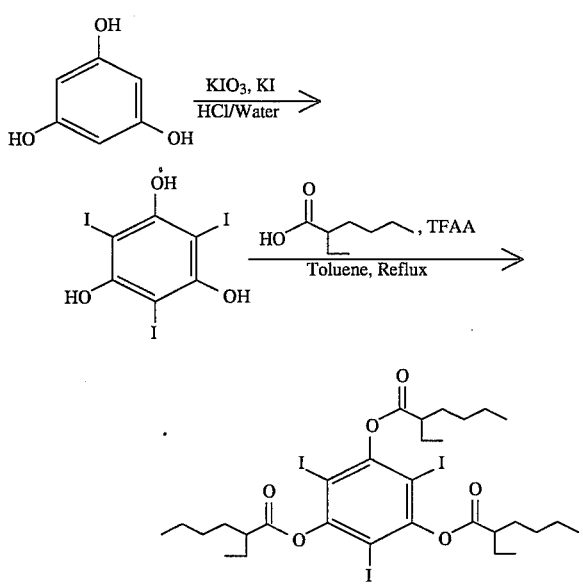

The method of F. L. Weitle, *J. Org. Chem.* 41, 2044–2045 (1976) was used to prepare 2,4,6-triiodophloroglucinol.

A mixture of 10.00 g (19.8 mmol) of 2,4,6-triiodophloroglucinol, 17.1 g (118.8 mmol) of 2-ethylhexanoic acid, 149.7 g (712.8 mmol) of trifluoroacetic anhydride and 50 ml of anhydrous toluene was refluxed for 18 hrs. The dark red solution was concentrated in vacuo to produce a brown oil. The oil was partitioned between 250 ml of ethyl acetate and 100 ml of 5% potassium carbonate solution and the ethyl acetate layer was washed with saturated sodium bicarbonate solution (100 ml), brine (50 ml) and dried over sodium sulfate. Concentration in vacuo produced a brown oil. The oil was purified by flash chromatography on 713 g of silica gel with 5% ethyl acetate/hexane as the eluent. Concentration in vacuo produced 16.25 g (93%) of product as a yellow oil.

Title Compound: $^1$H (300 MHz) and $^{13}$C (75 MHz) NMR spectra were consistent with the desired structure. FAB/MS: $(M+1)^+883$.

EXAMPLE 7
2,4,6-Triiodophenyl dodecanoate

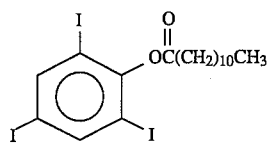

Dodecanoyl chloride (2.95 ml, 12.8 mmol) was added to a suspension of 2,4,6-triiodophenol (6.0 g, 12.7 mmol) in refluxing acetonitrile (50 ml) and the mixture was heated under argon for 24 hrs. The reaction mixture was cooled and washed with saturated aqueous sodium bicarbonate. The organic layer was dried over magnesium sulfate, filtered, and evaporated to dryness under vacuum to give an off-white solid. The crude product was recrystallized from methanol to give 6.9 g (83%) of the desired ester, mp 68°–69° C.

Title Compound: $^1$H (300 MHz) and $^{13}$C (75 MHz) NMR spectra were consistent with the desired structure. Calculated for $C_{18}H_{25}I_3O_2$: C, 33.05; H, 3.85; I, 58.20. Found: C, 32.91; H, 3.75; I, 58.25.

EXAMPLE 8
3-Trifluoromethyl-2,4,6-triiodophenyl 2-ethyl hexanoate

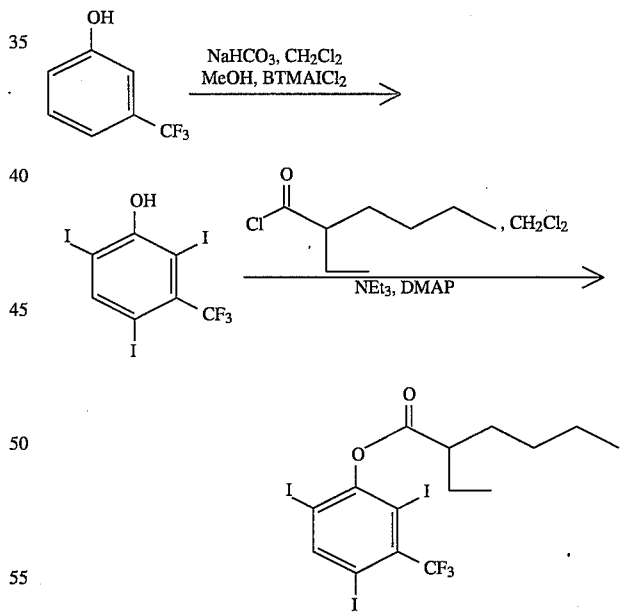

A mixture of 9.00 g (55.5 mmol) of α,α,α,-trifluoro-m-cresol, 31.4 g (374 mmol) of NaHCO$_3$ and 59.9 g (172 mmol) of benzyltrimethylammonium dichloroiodate in 78 ml dichloromethane/30 ml methanol was placed under nitrogen and stirred for 22 hrs. The mixture was filtered and the NaHCO$_3$ was washed with 200 ml of dichloromethane. The flitrate was washed with 1 M HCl (150 ml) 5% NaHSO$_3$ (100 ml) and brine (100 ml). The solution was dried over Na$_2$SO$_4$ and concentrated in vacuo to 27.1 g of brown solid. The solid was dissolved in a minimum amount of dichloromethane and was purified by flash chromatography on 678 g of silica gel with 30% dichloromethane/hexane as the eluent to afford 13.55 g (45%) of 3-trifluoromethyl-2,4,6-triiodophenyl 2-ethyl hexanoate as a pink solid. $^1$H-NMR (300 MHz) spectral data were consistent with the desired structure.

A mixture of 10.0 g (18.53 mmol) of 2,4,6-triiodo-3-trifluoromethyl phenol, 3.62 g (22.2 mmol) of 2-ethylhexanoyl chloride and 0.226 g (1.85 mmol) of 4-dimethylaminopyridine in 37 ml of dry dichloromethane was placed under nitrogen and cooled to 0° C. Triethylamine (2.25 g, 22.2 mmol) was added dropwise and the resulting solution was stirred for 16 hrs at room temperature. The mixture was partitioned between 200 ml of dichloromethane and 100 ml of 1 M HCl. The dichloromethane layer was washed with saturated NaHCO$_3$ solution (50 ml) and brine (100 ml). The solution was dried over Na$_2$SO$_4$ and concentrated in vacuo to 12.80 g of brown oil. The oil was purified by flash chromatography on 20 g of silica gel with 3% ethyl acetate/hexane as the eluent. Concentration in vacuo afforded 11.63 g (94%) of product as a light yellow oil.

Title Compound: $^1$H (300 MHz) and $^{13}$C (75 MHz) NMR spectra were consistent with the desired structure. FAB/MS: M$^+$666. Calculated for C$_{15}$H$_{16}$F$_3$I$_3$O$_2$: C, 27.05; H, 2.42; I 57.16. Found: C, 27.47; H, 2.42; I, 56.88.

EXAMPLE 9
2,4,6-Triiodophenyl-bis-(2-methylpentanoate)

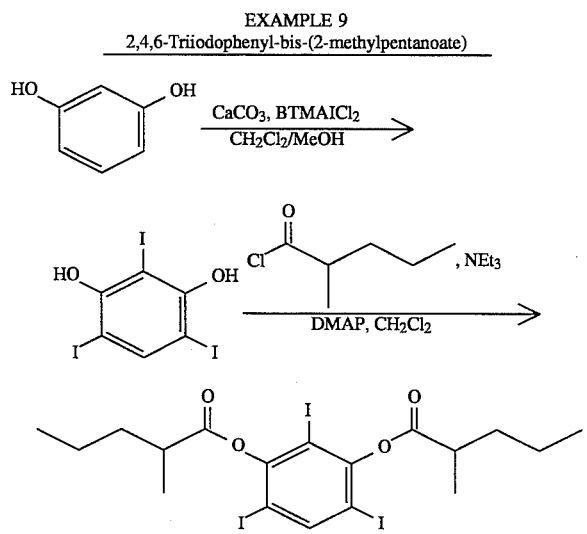

A mixture of 1.00 g (9.08 mmol) of resorcinol, 6.12 g (61.1 mmol) of calcium carbonate and 9.80 g (28.2 mmol) of benzyltrimethylammonium dichloroiodate (BTMAICl$_2$) in 13 ml dichloromethane/5 ml methanol was placed under nitrogen and stirred for 4 hrs. The mixture was filtered and concentrated in vacuo. The resulting residue was partitioned between 100 ml of ethyl acetate and 50 ml of saturated NaHCO$_3$ solution. The ethyl acetate layer was washed with brine (25 ml) and dried over Na$_2$SO$_4$. Concentration in vacuo produced a dark brown solid. The solid was dissolved in a minimum amount of ethyl acetate and was purified by flash chromatography on 100 g of silica gel with 20% ethyl acetate/hexane as the eluent. The first 125 ml to elute contained nothing while the pure product eluted with the next 224 ml. Concentration in vacuo afforded 2.78 g (63%) of 2,4,6-triiodoresorcinol as a cream colored solid. $^1$H-NMR (300 MHz) spectral data were consistent with the desired structure.

A mixture of 0.500 g (1.03 mmol) of 2,4,6-triiodoresorcinol and 0.304 g (2.26 mmol) of 2-methylpentanoyl chloride in 2 ml of dry dichloromethane was placed under nitrogen. A solution containing 0.207 g (2.05 mmol) of triethylamine and 0.125 g (1.03 mmol) dimethylaminopyridine in 2 ml of dry dichloromethane was added dropwise while stirring. After complete addition the resulting light brown solution was stirred 30 min under nitrogen. The solution was partitioned between 50 ml of dichloromethane and 50 ml of 1 M HCl. The dichloromethane layer was washed with saturated NaHCO$_3$ solution (50 ml) and brine (25 ml). The solution was dried over Na$_2$SO$_4$ and concentrated in vacuo to 0.677 g of brown oil. The oil was purified by flash chromatography on 20 g of silica gel with 5% ethyl acetate/hexane as the eluent. Concentration in vacuo afforded 0.622 g (88%) of product as a colorless oil which slowly solidified over seven days.

Title Compound: $^1$H (300 MHz) and $^{13}$C (75 MHz) NMR spectra were consistent with the desired structure. FAB/MS: (M+1)$^+$685. Calculated for C$_{18}$H$_{23}$I$_3$O$_4$: C, 31.60; H, 3.39. Found: C, 31.79; H, 3.32, mp 44.5°–47.0° C.

EXAMPLE 10
2,4,6-Triiodophenyl hexanesulfonate

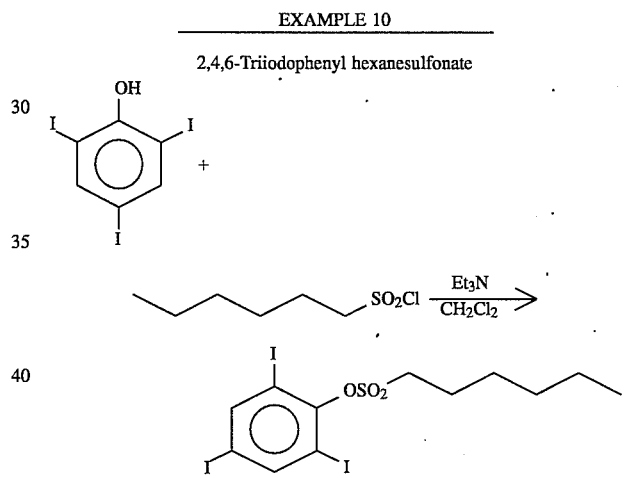

A solution of 10 g (0.021 mol) of 2,4,6-triiodophenol in 250 ml of methylene dichloride was stirred in an ice bath with 12.6 ml of triethylamine. To this solution was added dropwise 8.5 g (0.046 mol) of hexanesulfonyl chloride in 50 ml of methylene chloride. The reaction mixture was then stirred for 18 hrs at room temperature. Water was added and after separation, the organic layer was washed with saturated potassium carbonate and brine. The solution was dried over MgSO$_4$, filtered and concentrated to afford 13.5 g of crude product. Chromatography on 250 g of silica gel using 10% ethyl acetate/hexane afforded 9.8 g of product which upon recrystallization twice from hexane gave 6.5 g (50%) of 2,4,6-triiodophenyl hexanesulfonate, mp 70°–71° C.

Title Compound: $^1$H (300 MHz) and $^{13}$C (75 MHz) NMR spectra were consistent with the desired structure. MS; MH$^+$621, M$^+$620. Calculated for C$_{12}$H$_{15}$O$_3$SI$_3$: C, 23.47; H, 2.44; S, 5.17; I, 61.40. Found: C, 23.26; H, 2.31; S, 5.21; I, 61.32.

EXAMPLE 11
2,4,6-Triiodophenyl heptanesulfonate

Using the same procedure as for 2,4,6-triiodophenyl hexanesulfonate, 2,4,6-triiodophenyl heptanesulfonate was prepared from 15 g (0.032 mol) of 2,4,6-triiodophenol in 33% yield, mp 78°–80° C.

Title Compound: $^1$H (300 MHz) and $^{13}$C (75 MHz) NMR spectra were consistent with the desired structure. MS; MH$^+$635. Calculated for $C_{13}H_{17}O_3SI_3$: C, 24.63; H, 2.70; S, 5.06; I, 60.04. Found: C, 24.71; H, 2.59; S, 5.06; I, 59.96.

EXAMPLE 12
2,4,6-Triiodophenyl decanesulfonate

Using the same procedure as for 2,4,6-triiodophenyl hexanesulfonate without the chromatography step, 2,4,6-triiodophenyl decanesulfonate was prepared from 10 g (0.021 mol) of 2,4,6-triiodophenol in 59% yield, mp 71°–72° C.

Title Compound: $^1$H (300 MHz) and $^{13}$C (75 MHz) NMR spectra were consistent with the desired structure. MS; MH$^+$677. Calculated for $C_{16}H_{23}O_3SI_3$: C, 28.42; H, 3.43; I, 4.71; S, 56.31. Found: C, 28.47; H, 3.28; I, 4.73; S, 56.53.

The natural, pharmaceutically acceptable clays incorporated in the present invention comprise aluminum silicates. They are used in purified form, suitable for administration to patients. The natural, pharmaceutically acceptable clays of the present invention, generally referred to as smectities, consist of dioctohedral smectites and trioctahedral smectites.

Dioctahedral smectites include:

montmorillonite, having the formula $$M^+Al_{3-y}(FeMg)_ySi_4O_{10}(OH)_2 \cdot nH_2O;$$

beidelite, having the formula $$M^+(Al_2(Si_{4-x}Al_x)O_{10}(OH)_2 \cdot nH_2O;$$

nontronite, having the formula $$M^+(Fe_2^{3+}(Si_{4-x}Al_x)O_{10}(OH)_2 \cdot nH_2O;$$

wherein $M^+$ is Na, Ca or Mg.

Trioctahedral smectites include:

saponite, having the formula $$M^+(Mg_{3-y}(AlFe)_y)Si_{4-x}Al_xO_{10}(OH)_2 \cdot nH_2O; \text{ and}$$

hectorite, having the formula $$M^+(Mg_{3-y}Li_y)Si_4O_{10}(OH)_2 \cdot nH_2O;$$

wherein $M^+$ is Na, Ca or Mg.

The clays are available from chemical suppliers, such as, for example, American Colloid Company, Arlington Heights, Ill., under the tradenames:

MAGNABRITE®HS;
HECTABRITE®DP,
HECTABRITE®LT,
CARMARGO®White,
POLARGEL®NF,
POLARGEL®HV, and
VOLCLAY®NF-BC.

Other suppliers include: Engelhard Corp., Iselin, N.J.; Ashland Chemical Inc., Colombus, Ohio; RT Vanderbilt Co., Inc., Norwalk, Conn. and Whittaker Clark & Daniels, Inc., S. Plainfield, N.J.

The contrast agent and the pharmaceutically acceptable clay are formulated for administration using physiologically acceptable carriers or excipients in a manner within the skill of the art. The contrast agent with the addition of pharmaceutically acceptable aids (such as surfactants and emulsifiers) and excipients may be suspended or emulsified in an aqueous medium resulting in a suspension or emulsion.

COMPOSITIONS OF THE PRESENT INVENTION

Compositions of the present invention comprise the following pharmaceutically acceptable components based on % w/v:

| Ingredients | Broad Range | Preferred Range | Most Preferred Range |
|---|---|---|---|
| Contrast agent | 5–45 | 10–35 | 15–25 |
| Clay | 0.1–10 | 0.5–5 | 1–2 |
| Surfactant | 1–20 | 2–10 | 3–5 |
| Excipients | 0–15 | 0.5–5 | 1–2 |
| Water - q.s. to 100% by volume | | | |

Excipients contemplated by the present invention include antifoaming agents, such as simethicone, siloxyalkylene polymers and polyoxyalkylated natural oils; preservatives, such as methyl paraben, propyl paraben, benzoic acid and sorbic acid; flavoring/sweetening agents, such as sodium saccharine; and coloring agents, such as lakes and dyes.

While the iodophenyl esters and iodophenoxy sulfonates of the present invention in formulations with a pharmaceutically acceptable vehicle provide good quality x-ray images, the addition of a pharmaceutically acceptable clay to the formulations greatly increases the quality of the x-ray images. At the low extreme of the concentration range there is little or no benefit gained, while above the higher extreme of the concentration range the formulation is too viscous for administration.

The following formulation examples will further illustrate the invention.

Example 13

| Components | |
|---|---|
| 2,4,6-Triiodophenyl-2-ethylhexanoate | 22.00 g |
| HECTABRITE ® DP | 1.50 g |
| Sorbitan Monostearate | 0.70 g |
| Polysorbate 60 (Tween 60) | 1.20 g |
| Poloxamer 338 | 4.00 g |
| Sodium Saccharine | 0.30 g |
| Benzoic Acid | 0.50 g |

Example 13-continued

| Components | |
|---|---|
| Sorbic Acid | 0.05 g |
| Water q.s. to make 100 ml | |

Example 14

| Components | |
|---|---|
| 2,4,6-Triiodophenyl-tris-(2-ethylhexanoate) | 22.50 g |
| POLARGEL ® NF | 2.30 g |
| Sorbitan Mono-oleate | 0.45 g |
| Polysorbate 20 (Tween 820) | 1.30 g |
| Polyvinyl Alcohol | 4.50 g |
| Sodium Saccharine | 0.25 g |
| Simethicone emulsion (food-grade) | 0.10 g |
| Water q.s. to make 100 ml | |

Example 15

| Components | |
|---|---|
| 2,4,6-Triiodophenyl hexanesulfonate | 18.50 g |
| MAGNABRITE ® HS | 1.25 g |
| Sorbitan monopalmitate | 0.60 g |
| Polyoxyethylene myristyl ether | 0.60 g |
| Polyvinylpyrrolidone | 3.50 g |
| Vanilla flavoring (artificial) | 0.25 g |
| Strawberry flavoring (artificial) | 0.25 g |
| Sorbitol | 1.00 g |
| Water q.s. to make 100 ml | |

The surface active agents used in the present invention may be cationic, anionic, nonionic or zwitterionic.

Suitable cationic surfactants include cetyl trimethyl ammonium bromide, cetyl pyridinium chloride, myristyl gamma picolinium chloride and benzalkonium chloride. Suitable anionic agents include sodium lauryl sulphate, sodium heptadecyl sulphate, alkyl benzenesulphonic acids and salts thereof, sodium butylnapthalene sulfonate, and sulphosuccinates. Zwitterionic surface active agents are substances that when dissolved in water they behave as diprotic acids and, as they ionize, they behave both as a weak base and a weak acid. Since the two charges on the molecule balance each other out they act as neutral molecules. The pH at which the zwitterion concentration is maximum is known as the isoelectric point. Compounds, such as certain amino acids having an isoelectric point at the desired pH of the formulations of the present invention are useful in practicing the present invention.

In preparing the formulations of the present invention we prefer to use nonionic emulsifiers or surface active agents, which, similarly to the nonionic contrast agents, possess a superior toxicological profile to that of anionic, cationic or zwitterionic agents. In the nonionic emulsifying agents the proportions of hydrophilic and hydrophobic groups are about evenly balanced. They differ from anionic and cationic surfactants by the absence of charge on the molecule and, for that reason, are generally less irritating than the cationic or anionic surfactants. Nonionic surfactants include carboxylic esters, carboxylic amides, ethoxylated alkylphenols, ethoxylated aliphatic alcohols, ethylene oxide polymer or ethylene oxide/propylene oxide co-polymers polyvinylpyrrolidone and polyvinylalcohol.

One particular type of carboxylic ester nonionic surface active agents are the partial, for example mono-, esters formed by the reaction of fatty and resin acids, for example of about 8 to about 18 carbon atoms, with polyalcohols, for example glycerol, glycols such as mono-, di-, tetra- and hexaethylene glycol, sorbitan, and the like; and similar compounds formed by the direct addition of varying molar ratios of ethylene oxide to the hydroxy group of fatty acids.

Another type of carboxylic esters are the condensation products of fatty and resin partial acids, for example mono-, esters ethylene oxide, such as fatty or resin acid esters of polyoxyethylene sorbitan and sorbitol, for example polyoxyethylene sorbitan, mono-tall oil esters. These may contain, for example, from about 3 to about 80 oxyethylene units per molecule and fatty or resin acid groups of from about 8 to about 18 carbon atoms. Examples of naturally occurring fatty acid mixtures which may be used are those from coconut oil and tallow while examples of single fatty acids are dodecanoic acid and oleic acid.

Carboxylic amide nonionic surface active agents are the ammonia, monoethylamine and diethylamine amides of fatty acids having an acyl chain of from about 8 to about 18 carbon atoms.

The ethoxylated alkylphenol nonionic surface active agents include various polyethylene oxide condensates of alkylphenols, especially the condensation products of mono-alkylphenols or dialkylphenols wherein the alkyl group contains about 6 to about 12 carbon atoms in either branched chain or particularly straight chain configuration, for example, octyl cresol, octyl phenol or nonyl phenol, with ethylene oxide, said ethylene oxide being present in amounts equal to from about 5 to about 25 moles of ethylene oxide per mole of alkylphenol.

Ethoxylated aliphatic alcohol nonionic surface active agents include the condensation products of aliphatic alcohols having from about 8 to 18 carbon atoms in either straight chain or branched chain configuration, for example oleyl or cetyl alcohol, with ethylene oxide, said ethylene oxide being present in equal amounts from about 30 to about 60 moles of ethylene oxide per mole of alcohol.

Preferred nonionic surface active agents include:

(a) Sorbitan esters (sold under the trade name Span) having the formula:

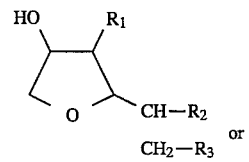

wherein $R_1=R_2=OH$, $R_3=R$ for sorbitan monoesters,
$R_1=OH$, $R_2=R_3=R$ for sorbitan diesters,
$R_1=R_2=R_3=R$ for sorbitan triesters,
where $R=(C_{11}H_{23})COO$ for laurate, $(C_{17}H_{33})COO$ for oleate, $(C_{15}H_{31})COO$ for palmitate, $(C_{17}H_{35})COO$ for stearate;

(b) Polyoxyethylene alkyl ethers (i.e. Brijs) having the formula:

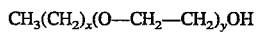

where (x+1) is the number of carbon atoms in the alkyl chain, typically:

| | |
|---|---|
| 12 lauryl | (dodecyl) |
| 14 myristyl | (tetradecyl) |
| 16 cetyl | (hexadecyl) |
| 18 stearyl | (octadecyl) | and y is the number of ethylene oxide groups in the hydrophilic chain, typically 10–60.

(c) Polyoxyethylene sorbitan fatty acid esters (Polysorbates 20, 40, 60, 65, 80 & 85 sold under the trade names of Tweens, Crillers, Sorlares and Monitans, having the formulas (1) and (2)

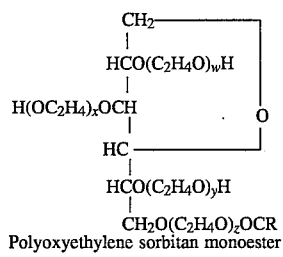

Polyoxyethylene sorbitan monoester

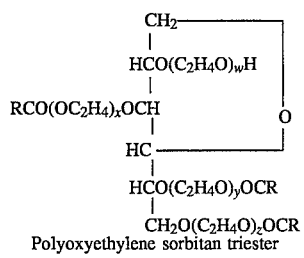

Polyoxyethylene sorbitan triester wherein w+x+y+z=20 (Polysorbate 20, 40, 60, 65, 80 and 85)

w+x+y+z=5 (Polysorbate 81)

w+x+y+z=4 (Polysorbate 21 and 61).

(d) Polyoxyethylene stearates, such as:

poly(oxy-1,2-ethanediyl), α-hydro-ω-hydroxy-octadecanoate; polyethylene glycol monostearate; and poly-(oxy-1,2-ethanediyl)-α-(1-oxooctadecyl)-ω-hydroxy-polyethylene glycol monostearate.

(e) Polyethylene oxide/polypropylene oxide block copolymers, sold under the name PLURONIC™, which include Poloxamer 407 (PLURONIC™ F127), Poloxamer 188 (PLURONIC™ F68), Poloxamer 237 (PLURONIC™ F87) and Poloxamer 338 (PLURONIC™ F108).

(f) Polyvinylpyrrolidone.

(g) Polyvinylalcohol.

The dosages of the contrast agent used according to the method of the present invention will vary according to the precise nature of the contrast agent used. Preferably, however, the dosage should be kept as low as is consistent with achieving contrast enhanced imaging. By employing as small amount of contrast agent as possible, toxicity potential is minimized. For most contrast agents of the present invention dosages will be in the range of from about 0.1 to about 16.0 g iodine/kg body weight, preferably in the range of from about 0.5 to about 6.0 g iodine/kg of body weight, and most preferably, in the range of from about 1.2 to about 2.0 g iodine/kg body weight for regular x-ray visualization of the GI tract. For CT scanning the contrast agents of the present invention will be in the range of from about 1 to about 600 mg iodine/kg body weight, preferably in the range of from about 20 to about 200 mg iodine/kg body weight, and most preferably in the range of from about 40 to about 80 mg iodine/kg body weight.

When administered to mammals, the compositions of the present invention produce excellent x-ray and CT images.

The invention, having been fully described, it will be apparent to one skilled in the art that changes and modifications can be made thereto without departing from the spirit and scope thereof.

What is claimed is:

1. An x-ray contrast composition for oral or retrograde examination of the gastrointestinal tract comprising on a % weight per volume basis:

(a) from about 5 to 45% of an x-ray contrast producing agent having the formula, or a pharmaceutically acceptable salt thereof

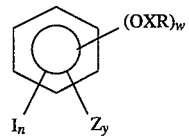

wherein

X is

or $-SO_2-$;

Z is H, halo, methyl, ethyl, n-propyl, $C_4$-$C_{20}$ alkyl, cycloalkyl, lower alkoxy, cyano, where the alkyl and cycloalkyl groups can be substituted with halogen or halo-lower-alkyl groups;

R is $C_1$-$C_{25}$ alkyl, cycloalkyl or aryl each of which may be optionally substituted with halo, fluoro-lower-alkyl, lower-alkoxy, hydroxy, carboxy or lower-alkoxy carbonyl; lower-alkenyl, lower-alkynyl, lower-alkylene or lower-alkoxy-carbonyloxy;

n is 1–5;

y is 0–4; and w is 1–4;

(b) from about 0.1 to 10% of a pharmaceutically acceptable clay selected from the group consisting of: montmorillonite, beidelite, nontronite, hectorite and saponite;

(c) from about 1.0 to 20% of a surfactant selected from the group consisting of nonionic, anionic, cationic and zwitterionic surfactants;

(d) from about 0 to 15% of an excipient; and (e) water to make 100% by volume.

2. The x-ray contrast composition of claim 1 wherein said x-ray contrast producing agent is present in an amount of from about 10 to 35%.

3. The x-ray contrast composition of claim 1 wherein said pharmaceutically acceptable clay constitutes from 0.5 to 5% of the composition.

4. The x-ray contrast composition of claim 1 wherein said surfactant constitutes from 2 to 10% of the composition.

5. The x-ray contrast composition of claim 1 wherein said excipient constitutes from 0.5 to 5% of the composition.

6. The x-ray contrast composition of claim 1 wherein said nonionic surface active agent is selected from the group consisting of carboxylic esters, carboxylic amides, ethoxylated alklyphenols, ethoxylated aliphatic alcohols, ethylene oxide polymer, ethylene oxide/propylene oxide copolymer, polyvinylpyrrolidone and polyvinylalcohol.

7. The x-ray contrast composition of claim 1 wherein said surfactant is sorbitan ester having the formula:

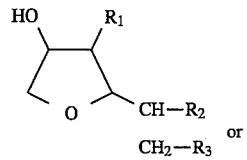

wherein $R_1=R_2=OH$, $R_3=R$ for sorbitan monoesters, $R_1=OH$, $R_2=R_3=R$ for sorbitan diesters, $R_1=R_2=R_3=R$ for sorbitan triesters, where $R=(C_{11}H_{23})COO$ for laurate, $(C_{17}H_{33})COO$ for oleate, $(C_{15}H_{31})COO$ for palmitate or $(C_{17}H_{35})COO$ for stearate.

8. The x-ray contrast composition of claim 1 wherein said surface active agent is polyoxyethylene stearate.

9. The x-ray contrast composition of claim 1 wherein said surfactant is polyoxyethylene sorbitan fatty acid ester of the formulas (1) and (2)

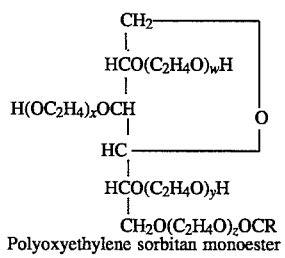

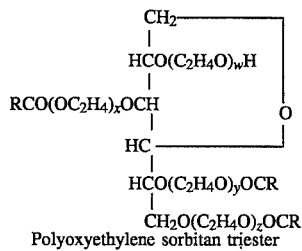

wherein w+x+y+z is selected from the group consisting of 20, 5, and 4.

10. The x-ray contrast composition of claim 1 wherein said x-ray contrast producing agent is selected from the group consisting of: 2,4,6-triiodophenyl-2-ethylhexanoate, 2,4,6-triiodophenyl-2-methylpentanoate, 2,4,6-triiodophenyl 3-cyclopentylpropionate, and 2,4,6-triiodophenyl (2-propyl)pentanoate.

11. The x-ray contrast composition according to claim 1 wherein said x-ray contrast agent is selected from the group consisting of: 2,4,6-triiodophenyl perfluoroheptanoate, 2,4,6-triiodophenyl-tris-(2-ethylhexanoate), 2,4,6-triiodophenyl dodecanoate, and 3-trifluoromethyl-2,4,6-triiodophenyl-2-ethylhexanoate.

12. The x-ray contrast composition according to claim 1 wherein said x-ray contrast agent is selected from the group consisting of: 2,4,6-triiodophenyl-bis-(2-methylheptanoate), 2,4,6-triiodophenyl hexanesulfonate, 2,4,6-triiodophenyl heptanesulfonate, and 2,4,6-triiodophenyl decanesulfonate.

13. A method of carrying out x-ray examination of the gastrointestinal tract of a patient, said method comprises the oral or rectal administration to the patient an x-ray contrast composition comprising:

(a) from about 5 to 45% of an x-ray contrast producing agent having the formula, or a pharmaceutically acceptable salt thereof

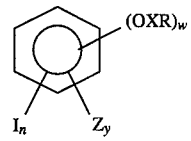

wherein

X is

or $-SO_2-$;

Z is H, halo, methyl, ethyl, n-propyl, $C_4$-$C_{20}$ alkyl, cycloalkyl, lower alkoxy, cyano, where the alkyl and cycloalkyl groups can be substituted with halogen or halo-lower-alkyl groups;

R is $C_1$-$C_{25}$ alkyl, cycloalkyl or aryl each of which may be optionally substituted with halo, fluoro-lower-alkyl, lower-alkoxy, hydroxy, carboxy or lower-alkoxy carbonyl; lower-alkenyl, lower-alkynyl, lower-alkylene or lower-alkoxy-carbonyloxy;

n is 1–5;

y is 0–4; and w is 1–4;

(b) from about 0.1 to 10% of a pharmaceutically acceptable clay selected from the group consisting of: montmorillonite, beidelite, nontronite, hectorite and saponite;

(c) from about 1.0 to 20% of a surfactant selected from the group consisting of nonionic, anionic, cationic and zwitterionic surfactants;

(d) from about 0.0 to 15% of an excipient; and (e) water to make 100% by volume.

14. The method of claim 13 wherein said x-ray contrast producing agent is present in an amount of from about 10 to 35%.

15. The method of claim 13 wherein said pharmaceutically acceptable clay constitutes from 0.5 to 5% of the composition.

16. The method of claim 13 wherein said surfactant constitutes from 2 to 10% of the composition.

17. The method of claim 13 wherein said excipient constitutes from 0.5 to 5% of the composition.

18. The method of claim 13 wherein said nonionic surface active agent is selected from the group consisting of carboxylic esters, carboxylic amides, ethoxylated alklyphenols, ethoxylated aliphatic alcohols, ethylene oxide polymer, ethylene oxide/propylene oxide co-polymer, polyvinylpyrrolidone and polyvinylalcohol.

19. The method of claim 13 wherein said surfactant is sorbitan ester having the formula:

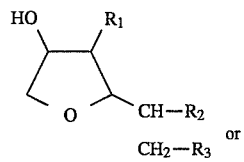

wherein $R_1=R_2=OH$, $R_3=R$ for sorbitan monoesters, $R_1=OH$, $R_2=R_3=R$ for sorbitan diesters, $R_1=R_2=R_3=R$ for sorbitan triesters, where $R=(C_{11}H_{23})COO$ for laurate, $(C_{17}H_{33})COO$ for oleate, $(C_{15}H_{31})COO$ for palmitate or $(C_{17}H_{35})COO$ for stearate.

20. The method of claim 13 wherein said surface active agent is polyoxyethylene stearate.

21. The method of claim 13 wherein said surfactant is polyoxyethylene sorbitan fatty acid ester of the formulas (1) and (2)

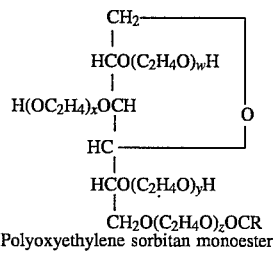
Polyoxyethylene sorbitan monoester

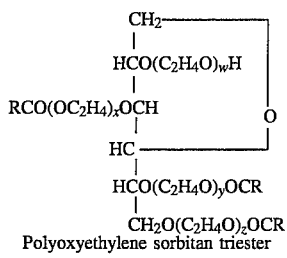
Polyoxyethylene sorbitan triester wherein w+x+y+z is selected from the group consisting of 20, 5, and 4.

22. The method of claim 13 wherein said x-ray contrast producing agent is selected from the group consisting of: 2,4,6-triiodophenyl 2-ethylhexanoate, 2,4,6-triiodophenyl 2-methylpentanoate, 2,4,6-triiodophenyl 3-cyclopentylpropionate, and 2,4,6-triiodophenyl (2-propyl)pentanoate.

23. The method of claim 13 wherein said x-ray contrast producing agent is selected from the group consisting of: 2,4,6-triiodophenyl perfluoroheptanoate, 2,4,6-triiodophenyl-tris-(2-ethylhexanoate), 2,4,6-triiodophenyl dodecanoate, and 3-trifluoromethyl-2,4,6-triiodophenyl 2-ethylhexanoate.

24. The method of claim 13 wherein said x-ray contrast producing agent is selected from the group consisting of: 2,4,6-triiodophenyl-bis-(2-methylheptanoate), 2,4,6-triiodophenyl hexanesulfonate, 2,4,6-triiodophenyl heptanesulfonate, and 2,4,6-triiodophenyl decanesulfonate.

* * * * *